United States Patent [19]

Keogh

[11] Patent Number: 5,728,420
[45] Date of Patent: Mar. 17, 1998

[54] OXIDATIVE METHOD FOR ATTACHMENT OF GLYCOPROTEINS TO SURFACES OF MEDICAL DEVICES

[75] Inventor: James R. Keogh, Maplewood, Minn.

[73] Assignee: Medtronic, Inc., Minneapolis, Minn.

[21] Appl. No.: 694,535

[22] Filed: Aug. 9, 1996

[51] Int. Cl.$^6$ .............................. B05D 3/10; A61L 33/00; A61L 27/00
[52] U.S. Cl. ...................... 427/2.12; 427/2.13; 427/2.24; 427/2.3; 427/2.31
[58] Field of Search .............................. 427/2.12, 2.13, 427/2.24, 2.28, 2.3, 2.31, 2.25

[56] References Cited

U.S. PATENT DOCUMENTS

| | | | |
|---|---|---|---|
| 3,826,678 | 7/1974 | Hoffman et al. | 117/81 |
| 4,308,254 | 12/1981 | Tayot et al. | 210/635 |
| 4,521,564 | 6/1985 | Solomon et al. | 525/54.1 |
| 4,600,652 | 7/1986 | Solomon et al. | 423/423.3 |
| 4,613,665 | 9/1986 | Larm | 536/20 |
| 4,642,242 | 2/1987 | Solomon et al. | 427/2 |
| 4,663,163 | 5/1987 | Hou et al. | 210/635 |
| 4,720,512 | 1/1988 | Hu et al. | 523/112 |
| 4,786,556 | 11/1988 | Hu et al. | 428/412 |
| 5,032,666 | 7/1991 | Hu et al. | 528/70 |
| 5,053,048 | 10/1991 | Pinchuk | 623/1 |
| 5,059,654 | 10/1991 | Hou et al. | 525/54.1 |
| 5,077,372 | 12/1991 | Hu et al. | 528/70 |
| 5,258,501 | 11/1993 | Barbaric et al. | 530/395 |
| 5,344,455 | 9/1994 | Keogh et al. | 623/11 |
| 5,362,852 | 11/1994 | Geoghegan | 530/345 |

OTHER PUBLICATIONS

R. G. Dickinson, et al., "A New Sensitive and Specific Test for the Detection of Aldehydes: Formation of 6–Mercapto–3–substituted–s–Traizolo[4,3–b]–s–Tetrazines," *Chem. Commun.*, 1719–1720 (1970) (No Month).

K.F. Geoghegan, et al., "Site–Directed Conjugation of Nonpeptide Groups to Peptides and Proteins via Periodate Oxidation of a 2–Amino Alcohol. Application to Modification at N–Terminal Serine," *Bioconjugate Chem.*, 3, 138–146 (1992) (No Month).

A.S. Hoffman, et al., "Covalent Binding of Biomolecules to Radiation–Grafted Hydrogels on Inert Polymer Surfaces," *Trans. Am. Soc. Artif. Intern. Organs*, 18, 10–18 (1972) (No Month).

S. Holmes, et al. "Amination of Ultra–High Strength Polyethylene Using Ammonia Plasma", *Composite Sciences & Technology* 38(1990) 21 (No Month).

Y. Ito, et al., "Materials for Enhancing Cell Adhesion by Immobilization of Cell–Adhesive Peptide," *J. Biomed. Mat. Res.*, 25, 1325–1337 (1991) (No Month).

P.H. O'Farrell, "High Resolution Two–Dimensional Electrophoresis of Proteins," *J. Biol. Chem.*, 250, 4007–4021 (1975) May.

*Primary Examiner*—Diana Dudash
*Attorney, Agent, or Firm*—Thomas F. Woods; Harold R. Patton

[57] ABSTRACT

A method for making a medical device having a glycoprotein immobilized on a substrate surface is provided. The method includes oxidizing 1,2 dihydroxy moieties with a periodate to form an aldehyde-functional material; combining the aldehyde-functional material with an amino-functional material to bond the two materials together through an imine moiety; and reacting the imine moiety with a reducing agent to form a secondary amine.

28 Claims, No Drawings

OXIDATIVE METHOD FOR ATTACHMENT OF GLYCOPROTEINS TO SURFACES OF MEDICAL DEVICES

BACKGROUND OF THE INVENTION

For many years, a number of medical devices (e.g., pacemakers, vascular grafts, stents, heart valves, etc.) that contact bodily tissue or fluids of living persons or animals have been developed, manufactured and used clinically. A major problem with such articles is that their surfaces tend to adsorb a layer of proteins from tissues and fluids such as tears, urine, lymph fluid, blood, blood products, and other fluids and solids derived from blood. The composition and organization of this adsorbed protein layer is thought to influence, if not control, further biological reactions. Adverse biological reactions such as thrombosis and inflammation can diminish the useful lifetime of many devices.

Implantable medical devices also tend to serve as foci for infection of the body by a number of bacterial species. These device-associated infections are promoted by the tendency of these organisms to adhere to and colonize the surface of the device. Consequently, it has been of great interest to physicians and the medical industry to develop surfaces that are less prone in promoting the adverse biological reactions that typically accompany the implantation of a medical device.

One approach for minimizing undesirable biological reactions associated with medical devices is to attach various biomolecules to their surfaces for the attachment and growth of a cell layer which the body will accept. Biomolecules such as growth factors, cell attachment proteins and cell attachment peptides have been used for this purpose. In addition, biomolecules such as antithrombogenics, antiplatelets, anti-inflammatories, antimicrobials and the like have also been used to minimize adverse biomaterial-associated reactions.

A number of approaches have been suggested to attach such biomolecules. These approaches typically require the use of coupling agents such as glutaraldehyde, cyanogen bromide, p-benzoquinone, succinic anhydrides, carbodiimides, diisocyanates, ethyl chloroformate, dipyridyl disulphide, epichlorohydrin, azides, among others, which serve as attachment vehicles for coupling of biomolecules to biomaterial surfaces. For example, covalent attachment of biomolecules using water soluble carbodiimides is described by Hoffman et al., "Covalent Binding of Biomolecules to Radiation-Grafted Hydrogels on Inert Polymer Surfaces", *Trans. Am. Soc. Artif. Intern. Organs*, 18, 10–18 (1972); and Ito et al., "Materials for Enhancing Cell Adhesion by Immobilization of Cell-Adhesive Peptide", *J. of Biomed. Mat. Res.*, 25, 1325–1337 (1991).

One type of biomolecule which is often coupled to biomaterial surfaces with coupling molecules is protein. Proteins are polypeptides made up of amino acid residues. In general, established coupling procedures couple proteins to substrate surfaces through a protein's lysine amino acid residues which contain terminal amino groups. This method of binding has several inherent problems. For example, if a number of lysine residues are present on a protein's surface, multiple attachments can occur. Multiple attachment sites can lead to multiple conformations of the protein on the biomaterial surface. The lack of coupling specificity can disrupt or destroy the biological activity of the protein being coupled. In addition, coupling molecules can add instability to the biomaterial surface and increase the prospect for burial of the attached protein in the coupling layer. Coupling molecules can also create nonspecific and undesirable crosslinks between protein molecules, thereby destroying the biological properties of the protein or they can create bonds amongst surface functional sites, thereby inhibiting attachment. The use of coupling molecules can also decrease the specificity for attachment of the protein to the biomaterial surface, thereby losing conformational control over the attachment process.

SUMMARY OF THE INVENTION

This invention provides an improved method for covalently attaching a biomolecule to substrate surface. Specifically, the present invention provides a method for making a medical device having a glycoprotein immobilized on a biomaterial surface. The method includes the steps of: combining a periodate with a glycoprotein comprising a 1,2 dihydroxy moiety to form an aldehyde-functional material; combining the aldehyde-functional material with a material comprising a primary amine moiety to bond the two materials together through an imine moiety; and reacting the imine moiety with a reducing agent to form an immobilized glycoprotein on a medical device biomaterial surface through a secondary amine linkage.

Preferably, the method involves the steps of: combining a periodate with a glycoprotein comprising a 1,2 dihydroxy moiety to form an aldehyde-functional material in an aqueous solution having a pH of about 4–9 and a temperature of about 50° C. combining the aldehyde-functional material with a biomaterial surface comprising a primary amine moiety to immobilize the glycoprotein on the substrate surface through an imine moiety; and reacting the imine moiety with a reducing agent to form an immobilized glycoprotein on the substrate surface through a secondary amine linkage.

The method of the present invention can also be used to crosslink glycoproteins comprising both a 1,2 dihydroxy moiety and a primary amine moiety. This method includes the steps of: combining a periodate with the glycoprotein to oxidize the 1,2 dihydroxy moiety to form an aldehyde moiety; allowing the aldehyde moiety to combine with the amine moiety forming an imine moiety; and reacting the imine moiety with a reducing agent to form a secondary amine and crosslinked material. This crosslinked material can be used as a substrate for coupling biomolecules. For example, aldehyde containing biomolecules can be attached to free amine moieties on the surface of the crosslinked material or amine containing biomolecules can be attached to free aldehyde moieties on the surface of the crosslinked material.

A "glycoprotein" may be defined as a conjugated protein which contains carbohydrate groups. A typical glycoprotein contains one or more oligosaccharide units linked to either asparagine amino acid residues by N-glycosidic bonds or serine or threonine amino acid residues by O-glycosidic bonds. The saccharide unit directly bonded to asparagine is typically N-acetylglucosamine, whereas N-acetylgalactosamine tends to be the saccharide unit bonded to serine or threonine residues. Oligosaccharides bond to glycoproteins can contain a variety of carbohydrate units. They also tend to be located at sites away from the biologically active site of the protein. Thus, oligosaccharide moieties of glycoproteins can typically be modified with little or no effect on the biological properties of the protein. The glycoproteins suitable for use in the present invention include at least one carbohydrate comprising a 1,2 dihydroxy moiety.

A "biomaterial" may be defined as a material that is designed and constructed to be placed in or onto the body or to contact fluid of the body. Ideally, a biomaterial will not induce undesirable reactions in the body such as blood clotting, tissue death, tumor formation, allergic reaction, foreign body reaction (rejection) or inflammatory reaction; will have the physical properties required to function for the intended purpose; can be purified, fabricated and sterilized easily; will substantially maintain its physical properties and function during the time that it remains implanted in or in contact with the body. The biomaterials suitable for use in the present invention include an amine moiety.

A "medical device" may be defined as a device that has surfaces that contact tissue, blood, or other bodily fluids in the course of their operation, which fluids are subsequently used in patients. This can include, for example, extracorporeal devices for use in surgery such as blood oxygenators, blood pumps, blood sensors, tubing used to carry blood and the like which contact blood which is then returned to the patient. This can also include endoprostheses implanted in blood contact in a human or animal body such as vascular grafts, stents, pacemaker leads, heart valves, and the like that are implanted in blood vessels or in the head. This can also include devices for temporary intravascular use such as catheters, guide wires, and the like which are placed into blood vessels or the head for purposes on monitoring or repair.

DETAIL DESCRIPTION OF THE INVENTION

This invention is aimed at solving a number of problems associated with the use of medical devices. The invention involves an oxidative process for covalently attaching glycoproteins to biomaterial surfaces for use in medical devices. The invention also provides an oxidative method for producing crosslinked materials.

Proteins that possess a carbohydrate bearing a 1,2 dihydroxy moiety are oxidizable with periodate, which can be provided as periodic acid or salts thereof, such as sodium periodate, potassium periodate, or other alkali metal periodates. Typically, a stoichiometric amount of periodate is used to oxidize the 1,2 dihydroxy moiety, although an excess could be used. Oxidation of such glycoproteins forms reactive aldehyde moieties within the glycoprotein.

The oxidation is carried out in an aqueous solution, preferably an aqueous buffered solution, at room temperature that does not destroy the biological properties of the glycoprotein. Generally, buffers having a pH in a range of about 4–9 can be used, with a pH of about 6–8 desired for certain pH sensitive glycoproteins. Generally, the oxidation is carried out at a temperature of about 0–50° C. and preferably at a temperature of about 4–37° C. Depending on the glycoprotein, oxidation reactions can be carried out for as short as a few minutes to as long as many days. Commonly, oxidation is complete within 24 hours. Long-term oxidation reactions are preferably performed in the dark to prevent "overoxidation ."

Treatment times and temperatures for the oxidation process tend to be inversely related. That is, higher temperatures require relatively shorter treatment times. The limitations of time and temperature are governed by the effect of the treatment on the biological stability of the glycoprotein. Treatment conditions outside the above said ranges are still within the scope of this invention. There is a wide latitude in determining the proper conditions for a particular system and these conditions can be readily determined by one skilled in the art by routine experimentation upon reading of the information presented herein.

Subsequent to oxidation, the reaction solution may be stored prior to attachment to a substrate at about 4° C. Typically, the storage stability of the reaction solution at a neutral pH or slightly acidic pH can extend for 1–14 days and sometimes even months when stored in the dark.

The resultant aldehyde moieties interact with sites on a biomaterial surface for covalent attachment of the glycoproteins. These biomaterial surface attachment sites comprise amine moieties, which react with aldehyde moieties forming imines. The substrate surface to which the glycoprotein is to be coupled should contain an adequate density of amine moieties for attaching the desired number of glycoproteins.

Biomaterials that do not contain amines on their surface can easily be aminated by a number of methods well known to those skilled in the art. For example, amines can be provided by plasma treating materials with ammonia gas as found in Holmes and Schwartz, "Amination of Ultra-high Strength Polyethylene using Ammonia Plasma", *Composites Science and Technology* 38, 1–21 (1990). Alternatively, amines can be provided by grafting acrylamide to the substrate followed by chemical modification to introduce amine groups by methods well known to those skilled in the art. Polyvinyl amines or polyalkylimines can also be covalently attached to polyurethane surfaces according to the method taught by U.S. Pat. No. 4,521,564 (Solomone et al.). Alternatively, for example, aminosilane can be attached to the surface as set forth in U.S. Pat. No. 5,053,048 (Pinchuk), a grafted acrylamide-containing polymer can be attached by radiation grafting as set forth in U.S. Pat. No. 3,826,678 (Hoffman et al.), a grafted N-(3-aminopropyl) methacrylamide-containing polymer can be attached by ceric ion grafting as set forth in U.S. Pat. No. 5,344,455 (Keogh et al.).

Typically, when a aldehyde moiety (RCHO) reacts with a primary amine moiety (R'NH2), an equilibrium is set up with the reaction product, which is a relatively unstable imine moiety (R'N=CHR). This coupling reaction can be carried out under the same conditions described above for the oxidation, which are designed to protect the glycoprotein from damage. To stabilize the linkage between the glycoprotein and the biomaterial surface, subsequent reductive alkylation of the imine moiety is carried out using reducing agents (i.e., stabilizing agents) such as, for example, sodium borohydride, sodium cyanoborohydride, and amine boranes, to form a secondary amine (R'NH—CH$_2$R). This reaction can also be carried out under the same conditions described above for the oxidation. Typically, however, the coupling and stabilizing reactions are carried out in a neutral or slightly basic solution and at a temperature of about 0°–50° C. Preferably, the pH is about 6–10, and the temperature is about 4°–37° C, for the coupling and stabilizing reactions. These reactions (coupling and stabilizing) can be allowed to proceed for just a few minutes or for many hours. Commonly, the reactions are complete (i.e., coupled and stabilized) within 24 hours.

Generally, glycoproteins used according to this invention can be, for example: anticoagulant and antithrombotic proteins; clotting proteins; platelet proteins; anti-inflammatory proteins; antibodies; immunoglobulins; defense proteins; enzymes; hormones; growth factors; globular proteins; blood proteins; regulatory proteins; transport proteins; fibrous proteins; structural proteins; membrane proteins; cell attachment proteins; proteoglycans; toxins; and ligands. The glycoproteins can be synthetically derived or naturally occurring. As long as the glycoprotein includes a 1,2 dihydroxy moiety, it can be attached to an aminated biomaterial surface by the method of the present invention.

Some glycoproteins are susceptible to conformational changes when brought into contact with a hydrophobic substrate surface. These conformational changes can lead to the exposure of internalized nonpolar groups which can lead to hydrophobic interactions between the glycoprotein and the surface. These hydrophobic interactions can cause the exclusion of water molecules that normally surround the glycoprotein in solution. This exclusion of water molecules between the protein and the surface strengthens the hydrophobic interaction and can cause further conformational change of the protein. The degree of conformational change a glycoprotein experiences may or may not destroy its biological properties. Therefore, one must take into account the hydrophobic nature of the substrate surface when attaching glycoproteins which are prone to hydrophobic interactions. In these cases, it is preferred to create a hydrophilic environment on the biomaterial surface, thereby preventing any unwanted hydrophobic interactions between the glycoprotein and the surface which can destroy the biological properties of the protein. There are a number of surface-derivatization techniques, e.g., grafting techniques, well known to those skilled in the art for creating hydrophilic substrate surfaces. For example, techniques based on ceric ion initiation, ozone exposure, corona discharge, UV irradiation and ionizing radiation ($^{60}$Co, X-rays, high energy electrons, plasma gas discharge) are known.

The substrates that can be modified by the method of the present invention include metals such as titanium/titanium alloys, TiNi (shape memory/super elastic), aluminum oxide, platinum/platinum alloys, stainless steels, MP35N, elgiloy, haynes 25, stellite, pyrolytic carbon, silver or glassy carbon; polymers such as polyamides, polycarbonates, polyethers, polyesters, polyolefins including polyethylenes or polypropylenes, polystyrenes, polyurethanes, polyvinyl chlorides, polyvinylpyrrolidones, silicone elastomers, fluoropolymers, polyacrylates, polyisoprenes, polytetrafluoroethylenes, and rubber; minerals or ceramics such as hydroxapatite; human or animal protein or tissue such as bone, skin, teeth, collagen, laminin, elastin or fibrin; organic materials such as wood, cellulose or compressed carbon; and other materials such as glass, or the like. Biomaterials made using these materials can be coated or uncoated, and derivatized or underivatized.

The method of the invention can be used to modify substrates of any shape or form including tubular, sheet, rod and articles of proper shape for use in a number of medical devices such as vascular grafts, aortic grafts, arterial, venous, or vascular tubing, vascular stents, dialysis membranes, tubing or connectors, blood oxygenator tubing or membranes, ultrafiltration membranes, intra-aortic balloons, blood bags, catheters, sutures, soft or hard tissue prostheses, synthetic prostheses, prosthetic heart valves, tissue adhesives, cardiac pacemaker leads, artificial organs, endotracheal tubes, lens for the eye such as contact or intraocular lenses, blood handling equipment, apheresis equipment, diagnostic and monitoring catheters and sensors, biosensors, dental devices, drug delivery systems, or bodily implants of any kind.

It will also be understood by one skilled in the art that glycoproteins or glycoprotein coatings can be crosslinked using the method of the present invention. That is, glycoproteins or glycoprotein coatings that contain both primary amine moieties and 1,2 dihydroxy moieties can be crosslinked to provide desired physical and biological properties. The resultant imines formed following the crosslinking of the aldehydes (as a result of oxidation of the 1,2 dihydroxy moieties) and amines contained within the substrate or substrate coating can be stabilized using a reducing agent as described above. For example, structural glycoproteins can be crosslinked to form a material that can be used as a substrate or a substrate coating. Also, glycoproteins, as described herein, can also be attached to the crosslinked material. Or amine containing glycoproteins can be attached to the aldehyde moieties in the crosslinked material.

An example of a material that can be used in all aspects of the present invention is fibrinogen. Fibrinogen, which is a structural protein, has oligosaccharides which can be oxidized with a source of periodate to form a pendant aldehyde moiety. The resultant aldehyde moieties can be used to crosslink the fibrinogen through bonds formed between the aldehydes and lysine residues contained on neighboring fibrinogen molecules. The resultant imine bonds can then be reduced using a mild reducing agent like sodium borohydride, sodium cyanoborohydride, or amine boranes. These crosslinks can endow fibrinogen and/or fibrin (thrombin polymerized fibrinogen) with desirable biological and/or physical properties such as mechanical strength, anti-immunogenicity, biostability, among others, without the use of a coupling agent. Thus, the method of the present invention eliminates the need for using glutaraldehyde, a commonly used cytotoxic coupling agent, to crosslink the fibrinogen or fibrin to control its physical and biological properties.

The aldehyde moieties formed by oxidation of fibrinogen/ fibrin can also be used to couple a variety of amine-containing biomolecules to a fibrinogen/fibrin substrate. Also, the ability to create aldehyde moieties along fibrinogen/fibrin molecules enables them to be covalently attached to amine containing substrate surfaces. Such fibrinogen/fibrin coated substrate surfaces can be used, for example, as cell seeding surfaces, cell binding surfaces, cell separating surfaces, fibrinogen/fibrin-coated stents, fibrinogen/fibrin-coated vascular grafts or fibrinogen/fibrin glues.

Although the examples described below involve treatment on polymeric films or tissue culture plates as the substrate surfaces, it is not intended that this invention be so limited.

EXAMPLE 1

PERIODATE OXIDATION OF BOVINE FIBRINOGEN

The glycoprotein bovine fibrinogen obtained from Sigma Chemical Co. (St. Louis, Mo.) was incubated in sodium metaperiodate (NaIO$_4$) also obtained from Sigma Chemical Co. (St. Louis, Mo.). The following four fibrinogen solutions were prepared to investigate the oxidation of fibrinogen with varying amounts of periodate: (1) 0.03 mM fibrinogen, 0.2 mM NaIO$_4$, 0.008M Na$_2$HPO$_4$, 0.002M KH$_2$PO$_4$, 0.14M NaCl, pH 7.4; (2) 0.03 mM fibrinogen, 0.1 mM NaIO$_4$, 0.008M Na$_2$HPO$_4$, 0.002M KH$_2$PO$_4$, 0.14M NaCl, pH 7.4; (3) 0.03 mM fibrinogen, 0.05 mM NaIO$_4$, 0.008M Na$_2$HPO$_4$, 0.002M KH$_2$PO$_4$, 0.14M NaCl, pH 7.4; and (4) 0.03 mM fibrinogen, 0.008M Na$_2$HPO$_4$, 0.002M KH$_2$PO$_4$, 0.14M NaCl, pH 7.4. The four fibrinogen solutions were incubated in the dark for 2 hours while shaking at room temperature. The resultant solutions, 500 µl of each, were added to 2 ml of a solution containing 0.8 g NaOH, 0.2 g 4-amino-3-hydrazino-5-mercato-1,2,4-triazole, which is available under the trade designation PURPALD from Sigma Chemical Co. (St. Louis, Mo.), in 20 ml deionized water, and shaken vigorously for 15 minutes at room temperature. Dickinson and Jacobsen, *Cem. Commun.*, 1719 (1970), described the specific and sensitive reaction of aldehydes with PURPALD to yield purple-to-magenta-colored 6-mercapto-s-triazolo-(4,3-b)-s-tetrazines. After the 15 minutes of shaking at room temperature, the resultant solutions were analyzed spectrophotometrically at 550 nm. Sample 4 was used as the blank. Sample absorbances obtained at 550 nm were 0.54 for sample 1, 0.53 for sample 2 and 0.51 for sample 3, which indicates that for all samples the fibrinogen was successfully oxidized forming aldehyde groups.

EXAMPLE 2

Periodate Oxidation of Bovine Vitronectin

The glycoprotein bovine vitronectin obtained from Sigma Chemical Co. (St. Louis, Mo.) was incubated in sodium metaperiodate ($NaIO_4$) also obtained from Sigma Chemical Co. (St. Louis, Mo.). The following two vitronectin solutions were prepared: (1) 0.001 mM vitronectin, 0.05M $NaIO_4$ and (2) 0.001 mM vitronectin. Both solutions were incubated in the dark for 2 hours while shaking at room temperature. The resultant solutions, 100 μl of each, were added to 2 ml PURPALD solution described in Example 1, and shaken vigorously for 30 minutes at room temperature. After the 30 minutes of shaking at room temperature, the resultant solutions were analyzed spectrophotometrically at 550 nm. The PURPALD solution was used as the blank. Sample absorbances obtained at 550 nm were 0.09 for sample 1 and 0.04 for sample 2, which indicated that vitronectin was successfully oxidized with forming aldehyde groups.

EXAMPLE 3

Periodate Oxidation of Bovine Fibronectin

The glycoprotein bovine fibronectin obtained from Sigma Chemical Co. (St. Louis, Mo.) was incubated in sodium metaperiodate ($NaIO_4$) also obtained from Sigma Chemical Co. (St. Louis, Mo.). The following two fibronectin solutions were prepared: (1) 0.002 mM fibronectin, 0.05M $NaIO_4$, 0.5M NaCl, 0.05M Tris, pH 7.5; and (2) 0.002 mM fibronectin, 0.5M NaCl, 0.05M Tris, pH 7.5. Both solutions were incubated in the dark for 2 hours while shaking at room temperature. The resultant solutions, 100 μl of each, were added to 2 ml PURPALD solution describe in Example 1 and shaken vigorously for 30 minutes at room temperature. After 30 minutes of shaking at room temperature, the resultant solutions were analyzed spectrophotometrically at 550 nm. Following an initial analysis, sample 1 was observed to contain to many aldehydes to measure. Therefore, sample 1 was diluted 1:50 in deionized water to achieve a measurable amount of aldehydes contained in the sample solution. The PURPALD solution was used as the blank. Sample absorbances obtained at 550 nm were 0.81 for sample 1 and 0.0 for sample 2, which indicate that the fibronectin in sample 1 was successfully oxidized forming aldehyde groups. Fibronectin in sample 2 was not oxidized due to the omission of periodate.

EXAMPLE 4

Attachment of Fibronectin to Aminated Substrates

Fibronectin was covalently attached to a substrate surface. The attachment technique began with the graft copolymerization of acrylamide (AAm) and N-(3-aminopropyl) methacrylamide (APMA) monomers onto an ozone treated polystyrene tissue culture plate with ceric ($Ce^{IV}$) ions. The $Ce^{IV}$ ions create free radicals on the ozone treated surface which initiate the graft copolymerization of the acrylamides. The amount of surface amination (the graft copolymerization of APMA and AAm) that took place on the substrate surface was measured via staining with ponceau S dye, a negatively charged dye molecule. Following grafting, fibronectin was coupled to the amine containing derivatized substrate surface. Fibronectin was first oxidized with sodium metaperiodate ($NaIO_4$) forming reactive aldehyde groups. These aldehyde groups were then used to covalently attached fibronectin to the primary amino groups present on the substrate surface. Sodium cyanoborohydride ($NaCNBH_3$) was then used to stabilize the imine linkages. The specific procedures for each of these steps are described below.

Polystyrene 24 well tissue culture plates were ozone treated by placing the culture plates in an ozone reaction vessel for 30 minutes while oxygen, which contained ozone, was flowing at a rate of 1.3 $cm^3$/min. The oxygen containing ozone was created by flowing the oxygen through a corona discharge apparatus, which exposes the flowing oxygen to an 8000V electrical potential. Following ozone treatment, the plates were soaked in nitrogen purged deionized water for 30 minutes at room temperature. Following the 30 minute soak in nitrogen purged deionized water, the plates were grafted with acrylamide (AAm) and N-(3-aminopropyl)methacrylamide (APMA) monomers (Eastman Kodak Co., Rochester, N.Y.) using ammonium cerium (IV) nitrate (Aldrich Chemical Co., Milwaukee, Wis.). The grafting solution consisted of 11.2 M AAm, 1.1M APMA, 400 mM nitric acid and 40 mM ammonium cerium (IV) nitrate in deionized water. The plates were allowed to graft for 3 hours in a 65° C. nitrogen purged oven. Following grafting the plates are rinsed vigorously with deionized water. The grafted plates were then tested with ponceau S dye. Following staining, the ponceau S dye was released from the surface using a 1% sodium dodecyl sulphate (SDS) solution and quantified spectrophotometrically at 520 nm. Sample absorbances obtained at 520 nm were 0.00 for nonderivatized plates and 1.44 for surface-derivatized plates. As the results demonstrate, the surface-derivatized plates contain primary amines on their surfaces.

Bovine fibronectin obtained from Sigma Chemical Co. (St. Louis, Mo.) was then incubated in sodium metaperiodate ($NaIO_4$) also obtained from Sigma Chemical Co. (St. Louis, Mo.). The following fibronectin solution was prepared: 0.002 mM fibronectin, 0.05M $NaIO_4$, 0.5M NaCl, 0.05M Tris, pH 7.5. The solution was incubated in the dark for 2 hours while shaking at room temperature. Sodium cyanoborohydride (1 mg/ml) was then added to the fibronectin solution. The resultant solution was immediately added to each of the amine containing surface-derivatized tissue culture plate wells (approximately 1 ml solution/well). The fibronectin solution incubated in the derivatized tissue culture plate wells overnight at room temperature. Following incubation, the wells were then vigorously rinsed with phosphate buffered saline (PBS) solution. The attachment of fibronectin to the amine containing surface-derivatized tissue culture plate surfaces was assessed using toluidine blue dye, a positively charged dye molecule. This dye ionically associates with the negative charges on a substrate surface. Therefore, the binding of toluidine blue dye to the fibronectin-derivatized surface is due to fibronectin's negative charges. The wells of each plate were filled with a 1% toluidine blue dye in deionized water solution. After a 5 minute incubation at room temperature, the dye solution was removed and the wells were thoroughly rinsed with PBS. The surface associated dye in each well was then eluted by mechanically shaking the plates in a 1% SDS in deionized water solution overnight. The amount of dye eluted from the wells was then determined spectrophotometrically at 630 nm. Sample absorbances obtained at 630 nm were 0.05 for the nonderivatized sample plate, 0.54 for the AAm/APMA-derivatized sample plate and 1.83 for the fibronectin-derivatized sample plate, which indicate that the fibronectin was successfully oxidized and then covalently attached to the substrate surface.

EXAMPLE 5

ELISA and Cellular Adherence to Fibronectin Coupled Surfaces

Polyurethane in the form of Pellethane 2363-55D was obtained from Dow Chemical Co. (Midland, Mich.) and extruded into film. The film was then cut into 1 cm$^2$ sample disks. Sample disks were then cleansed with ethanol and surface grafted with AAm and APMA monomers using Ce$^{IV}$ ion. The grafting solution consisted of 11.2M AAm, 1.1M APMA, 400 mM nitric acid and 40 mM ammonium cerium (IV) nitrate in deionized water. The sample disks were placed into the grafting solution and allowed to graft for 1 hour at room temperature. Following grafting, the sample disks were thoroughly washed with deionized water. Fibronectin was then coupled to the resultant APMN/AAm surface-derivatized sample disks via two methods.

The first method or peroxide method included the oxidation of fibronectin by sodium metaperiodate. Fibronectin (0.1 mg/ml) was exposed in the dark to a 1 µg/ml sodium metaperiodate in deionized water solution for 3 hours at room temperature. The APMN/AAm-derivatized sample disks were then placed into the oxidized fibronectin solution for 24 hours at room temperature. Sample disks were then thoroughly rinsed with deionized water. The samples were then incubated for 24 hours at room temperature in a 3 mg/ml sodium cyanoborohydride in deionized water solution. Sample disks were then thoroughly rinsed with deionized water.

The second method used glutaraldehyde as a coupling agent. The method included soaking the APMA/AAm-derivatized sample disks in a 2% glutaraldehyde in deionized water solution for 2 hours at room temperature. Sample disks were then thoroughly rinsed with deionized water. Following rinsing, the sample disks were then incubated in a 0.1 mg/ml fibronectin in deionized water solution for 24 hours at room temperature. Sample disks were then thoroughly rinsed with deionized water. The sample disks were then incubated for 24 hours at room temperature in a 3 mg/ml sodium cyanoborohydride in deionized water solution. Sample disks were then thoroughly rinsed with deionized water.

An enzyme linked immunosorbent assay (ELISA) was then performed to determine the ability of an antibody to recognize the fibronectin which had been coupled to the sample surfaces. Sample disks were washed for 20 minutes at room temperature with wash buffer (pH 7.4) consisting of 10 mM Tris, 0.15M NaCl and 0.05% Tween. Sample disks were then incubated at 37° C. for 30 minutes in blocking buffer (pH 7.4) consisting of 10 mM Tris, 0.15M NaCl, 0.05% Tween and 0.05% gelatin followed by three 10 minute washes with wash buffer. Next, sample disks were incubated at 37° C. for 1 hour in a primary antibody solution (pH 7.4) consisting of 10 mM Tris, 0.15M NaCl and 2 µg/ml mouse monoclonal anti-fibronectin antibody (Sigma Chemical Co., St. Louis, Mo.). Sample disks were then rinsed thrice (10 minutes per wash) with wash buffer. Next, sample disks were incubated at 37° C. for 1 hour in a peroxidase-labeled secondary antibody solution (pH 7.4) consisting of 10 mM Tris, 0.15M Nacl and 0.5 ng/ml anti-mouse IgG peroxidase antibody conjugate (Sigma Chemical Co., St. Louis, Mo.). Sample disks were then rinsed thrice (10 minutes per wash) with wash buffer. Sample disks were then incubated for 15 minutes at room temperature in a phosphate-citrate buffer (pH 5.0) containing 0.4 mg/ml o-phenyldiamine dihydrochloride and 0.2 µl/ml 30% hydrogen peroxide. The phosphate-citrate buffer consisted of 50 mM dibasic sodium phosphate and 25 mM citric acid in deionized water. Following the 15 minute incubation, the peroxide reaction was stopped with 3M HCl and the absorbance of the resultant solution was measured spectrophotometrically at 492 nm. The APMA/AAm-derivatized sample disks were used as controls for this experiment. Sample absorbances obtained from the spectrophotometric analysis were 0.016±0.038 for APMN/AAm-derivatized samples which contained glutaraldehyde coupled fibronectin and 0.204±0.068 for APMA/AAm-derivatized samples which contained periodate oxidized fibronectin. The results indicate that the periodate oxidation method was more successful at attaching fibronectin to the sample surfaces.

A cellular adherence assay was also performed to determine the ability of cells to adhere to fibronectin-derivatized sample surfaces sample disks were incubated for 1 hour at 37° C. in a blocking buffer consisting of 2 mg/ml ovalbumin in phosphate buffered saline (PBS), pH 7.4. Mouse fibroblasts (C3T3) obtained from American Type Culture Collection (Rockville, Md.) and maintained in Dulbecco's modified Eagle's medium (DMEM) supplemented with 10% fetal bovine serum were harvested using trypsin:EDTA and resuspended in serum-free DMEM containing 2 mg/ml ovalbumin. The cells were then washed twice, counted and resuspended to a final density of 5×04$^4$ cells/ml in serum-free DMEM containing 2 mg/ml ovalbumin. Sample disks were then incubated in the cell suspension for 1 hour at 37° C. Nonadherent cells were removed by a PBS wash. Sample disks were then fixed in 3% paraformaldehyde solution for 30 minutes. Adherent cells were then stained with a staining solution consisting of 1% toluidine blue dye and 3% paraformaldehyde in PBS. Following staining, sample surfaces were then examined for cellular adherence using a light microscope. Upon examination, APMN/AAm-derivatized samples and APMN/AAm-derivatized samples which contained glutaraldehyde coupled fibronectin appeared to have no adherent cells. In contrast, cells appeared adherent to APMA/AAm-derivatized samples which contained periodate oxidized fibronectin.

EXAMPLE 6

Crosslinking of Fibrinogen

Porcine fibrinogen obtained from Sigma Chemical Co. (St. Louis, Mo.) was incubated in sodium metaperiodate (NaIO$_4$) also obtained from Sigma Chemical Co. (St. Louis, Mo.) and sodium cyanoborohydride (NaCNBH$_3$) obtained from Aldrich Chemical Co. (Milwaukee, Wis.). The following fibrinogen solution was prepared: 0.03 mM fibrinogen, 0.02M NaIO$_4$, 0.02M NaCNBH$_3$, 0.008M Na$_2$HPO$_4$, 0.002M KH$_2$PO$_4$, 0.14M Nacl, pH 7.4. The solution was then shaken vigorously and placed into a 24 well tissue culture plate (approximately 1 ml of fibrinogen solution/ well). The plate was then incubated in the dark for 2 hours while shaking at room temperature. After 2 hours, the solution was observed to have become cloudy and very viscous indicating the fibrinogen had crosslinked. The sample was then shaken for an additional 22 hours in the dark. Following incubation, the crosslinked fibrinogen was tested for residual aldehydes using the PURPALD solution describe in Example 1. The results of the PURPALD assay demonstrated few residual aldehydes were present which indicated the formation of covalent crosslinks between the aldehydes and the amines present along the fibrinogen molecules.

The following bovine fibrinogen (Sigma Chemical Co., St. Louis, Mo.) solution was prepared: 0.02 mM fibrinogen, 0.008M $Na_2HPO_4$, 0.002M $KH_2PO_4$, 0.14M Nacl, pH 7.4. Following preparation, the solution was divided into four equal portions. Sodium metaperiodate (0.05 mM) was then added to samples 3 and 4. All four fibrinogen solutions were then incubated in the dark for 2 hours while shaking at room temperature. Next, 0.02 mM $NaCNBH_3$ was added to samples 2 and 4. Again, all four fibrinogen solutions were allowed to react for 2 hours while shaking at room temperature. The samples, 50 μl of each, were then placed into 450 μl of SDS-PAGE buffer solution consisting of 62.5 mM Tris-HCL, 5% β-mercaptoethanol, 10% glycerol and 2.3% SDS. Samples were then boiled for 3 minutes. The samples, 10 μl of each, were then loaded onto a 4–15% gradient gel and SDS-PAGE was performed according to the procedures described in O'Farrell, "High Resolution Two-dimensional Electrophoresis of Proteins", *J. Biol. Chem.* 250, 4007–4021 (1974). Following electrophoresis, the gel was stained with Coomassie Brilliant Blue, and the identity of the eluted proteins was determined by reference to molecular weight standards included on the gel. The results from SDS-PAGE indicated that the fibrinogen molecules in sample 4 had formed stable covalent crosslinks. In contrast, the results demonstrated that the fibrinogen molecules in the samples which contained no $NalO_4$ had formed no crosslinks.

It will be appreciated by those skilled in the art that while the invention has been described above in connection with particular embodiments and examples, the invention is not necessarily so limited and that numerous other embodiments, examples, uses, modifications and departures from the embodiments, examples and uses are intended to be encompassed by the claims attached hereto. The entire disclosure of each patent and publication cited herein is incorporated by reference, as each were individually incorporated by reference.

What is claimed is:

1. A method of forming a coating on a surface of a medical device, the coating imparting biocompatibility characteristics to the surface, the method comprising the ordered steps of:

(a) combining a periodate with a glycoprotein, the glycoprotein comprising a 1,2 dihydroxy moiety, to oxidize the 1,2 dihydroxy moiety to form an aldehyde-functional material;

(b) providing the medical device, the device having a suitable biomaterial forming the surface, an amine moiety being disposed on the surface;

(c) combining the aldehyde-functional material with the amine moiety to bond the aldehyde-functional material to the amine moiety and thereby form an imine moiety; and (d) reacting the imine moiety with a reducing agent to form an amine linkage, the amine linkage immobilizing the glycoprotein on the surface, the immobilized glycoprotein forming the coating.

2. The method of claim 1 wherein the device is selected from the group consisting of an implantable medical device, a blood oxygenator, a blood pump, tubing for carrying blood, a vascular graft, a stent, a pacemaker lead, a heart valve, a catheter and a guide wire.

3. The method of claim 1 wherein the glycoprotein is selected from the group consisting of an anticoagulant protein, an antithrombotic protein, a clotting protein, a platelet protein, an anti-inflammatory protein, an antibody, an immunoglobulin, a defense protein, an enzyme, a hormone, a growth factor, a globular protein, a blood protein, a regulatory protein, a transport protein, a fibrous protein, a structural protein, a membrane protein, a cell attachment protein, a proteoglycan, a toxin and a ligand.

4. The method of claim 1 wherein the glycoprotein is a naturally occurring glycoprotein.

5. The method of claim 1 wherein at least a portion of the surface forms at least one of a tube, a rod, a membrane, a balloon, a bag and a sheet.

6. The method of claim 5 wherein the surface comprises at least one of a biocompatible material selected from the group consisting of metal, titanium, titanium alloys, tin-nickel alloys, shape memory alloys, aluminum oxide, platinum, platinum alloys, stainless steel, MP35N stainless steel, elgiloy, stellite, pyrolytic carbon, silver carbon, glassy carbon, polymer, polyamide, polycarbonate, polyether, polyester, polyolefin, polyethylene, polypropylene, polystyrene, polyurethane, polyvinyl chloride, polyvinylpyrrolidone, silicone elastomer, fluoropolymer, polyacrylate, polyisoprene, polytetrafluoroethylene, rubber, ceramic, hydroxapatite, human protein, human tissue, animal protein, animal tissue, bone, skin, teeth, collagen, laminin, elastin, fibrin, wood, cellulose, compressed carbon and glass.

7. The method of claim 1 wherein the periodate comprises at least one of periodic acid, sodium periodate, alkali metal periodates and potassium periodate.

8. The method of claim 1 wherein the reducing agent comprises at least one of sodium borohydride, sodium cyanoborohydride and amine borane.

9. The method of claim 1 wherein the periodate is combined with the 1,2 dihydroxy moiety in an aqueous solution having a pH between about 4 and about 9.

10. The method of claim 1 wherein the periodate is combined with the 1,2 dihydroxy moiety in an aqueous solution having a temperature between about 0 and about 50 degrees Celisius.

11. The method of claim 1 wherein the aldehyde-functional material and the amine-functional material are combined in an aqueous solution having a pH between about 6 and about 10.

12. The method of claim 1 wherein the aldehyde-functional material and the amine-functional material are combined in an aqueous solution having a temperature between about 0 and about 50 degrees Celisius.

13. The method of claim 1 wherein the reducing agent is combined with the imine moiety in an aqueous solution having a pH between about 6 and about 10.

14. The method of claim 1 wherein the reducing agent is combined with the imine moiety in an aqueous solution having a temperature between about 0 and about 50 degrees Celisius.

15. A method of crosslinking a coating on a surface of a medical device, the coating imparting biocompatibility characteristics to the surface, the method comprising the ordered steps of:

(a) immobilizing a glycoprotein on the surface, the glycoprotein forming the coating and comprising a 1,2 dihydroxy moiety and an amine moiety;

(b) applying a periodate to the coating to oxidize the 1,2 dihydroxy moiety to form an aldehyde moiety;

(c) allowing the aldehyde moiety to combine with the amine moiety to form an imine moiety; and (d) reacting the imine moiety with a reducing agent to form a secondary amine and thereby cause at least portions of the coating to crosslink.

16. The method of claim 15 wherein the device is selected from the group consisting of an implantable medical device, a blood oxygenator, a blood pump, tubing for carrying blood, a vascular graft, a stent, a pacemaker lead, a heart valve, a catheter and a guide wire. material comprising a 1,2 dihydroxy moiety and a primary amine moiety comprises a glycoprotein.

17. The method of claim 15 wherein the glycoprotein is selected from the group consisting of an anticoagulant protein, an antithrombotic protein, a clotting protein, a platelet protein, an anti-inflammatory protein, an antibody, an immunoglobulin, a defense protein, an enzyme, a hormone, a growth factor, a globular protein, a blood protein, a regulatory protein, a transport protein, a fibrous protein, a structural protein, a membrane protein, a cell attachment protein, a proteoglycan, a toxin and a ligand.

18. The method of claim 15 wherein the glycoprotein is a naturally occurring glycoprotein.

19. The method of claim 15 wherein the periodate comprises at least one of periodic acid, sodium periodate, alkali metal periodates and potassium periodate.

20. The method of claim 15 wherein the reducing agent comprises at least one of sodium borohydride, sodium cyanoborohydride and amine borane.

21. The method of claim 15 wherein the periodate is combined with 1,2 dihydroxy moiety and the amine moiety in an aqueous solution having a pH between about 4 and about 9.

22. The method of claim 15 wherein the periodate is combined with the 1,2 dihydroxy moiety and a primary amine moiety in an aqueous solution having a temperature between about 0 and about 50 degrees Celisius.

23. The method of claim 15 wherein the reducing agent is combined with the material comprising an imine moiety in an aqueous solution having a pH between about 6 and about 10.

24. The method of claim 15 wherein the reducing agent is combined with the imine moiety in an aqueous solution having a temperature between about 0 and about 50 degrees Celisius.

25. The method of claim 1 wherein the oxidizing step is performed in the absence of light.

26. The method of claim 15 wherein the oxidizing step is performed in the absence of light.

27. The method of claim 15 wherein at least a portion of the surface forms at least one of a tube, a rod, a membrane, a balloon, a bag and a sheet.

28. The method of claim 15 wherein the surface comprises a biocompatible material selected from the group consisting of metal, titanium, titanium alloys, tin-nickel alloys, shape memory alloys, aluminum oxide, platinum, platinum alloys, stainless steel, MP35N stainless steel, elgiloy, stellite, pyrolytic carbon, silver carbon, glassy carbon, polymer, polyamide, polycarbonate, polyether, polyester, polyolefin, polyethylene, polypropylene, polystyrene, polyurethane, polyvinyl chloride, polyvinylpyrrolidone, silicone elastomer, fluoropolymer, polyacrylate, polyisoprene, polytetrafluoroethylene, rubber, ceramic, hydroxapatite, human protein, human tissue, animal protein, animal tissue, bone, skin, teeth, collagen, laminin, elastin, fibrin, wood, cellulose, compressed carbon and glass.

* * * * *